(12) United States Patent
Butler et al.

(10) Patent No.: US 7,338,454 B2
(45) Date of Patent: Mar. 4, 2008

(54) BREATH TEST

(75) Inventors: Ross Butler, North Adelaide (AU);
David Tivey, North Adelaide (AU);
Geoffrey Davidson, North Adelaide (AU); Nicole Pelton, North Adelaide (AU)

(73) Assignee: Children, Youth and Women's Health Service Incorporated, North Adelaide (AU)

( * ) Notice: Subject to any disclaimer, the term of this patent is extended or adjusted under 35 U.S.C. 154(b) by 301 days.

(21) Appl. No.: 10/497,192
(22) PCT Filed: Dec. 9, 2002
(86) PCT No.: PCT/AU02/01666
§ 371 (c)(1),
(2), (4) Date: Jun. 24, 2005
(87) PCT Pub. No.: WO03/048765
PCT Pub. Date: Jun. 12, 2003

(65) Prior Publication Data
US 2005/0245835 A1    Nov. 3, 2005

(30) Foreign Application Priority Data
Dec. 7, 2001    (AU) .................................... PR 9344

(51) Int. Cl.
*A61B 5/02*    (2006.01)
*G01N 1/22*    (2006.01)
*G01N 33/00*    (2006.01)
*G01N 33/497*    (2006.01)
*B32B 5/02*    (2006.01)
*B32B 27/04*    (2006.01)
*B32B 27/12*    (2006.01)

(52) U.S. Cl. ........................... 600/532; 73/23.3; 422/84
(58) Field of Classification Search ................. None
See application file for complete search history.

(56) References Cited

U.S. PATENT DOCUMENTS 5,711,306 A * 1/1998 Guilluy ...................... 600/543
5,924,995 A   7/1999 Klein et al.
6,186,958 B1 * 2/2001 Katzman et al. ............ 600/532

OTHER PUBLICATIONS

Abstract, M Hiele et al, "Measurement of the rate of assimilation of oligo- and polysaccharides by 13CO2 breath tests and isotope ratio mass spectrometry," Biomedical Environmental Mass Spectrometry, Oct. 1988, (1-12) pp. 133-135.*

(Continued)

*Primary Examiner*—Robert L. Nasser
(74) *Attorney, Agent, or Firm*—Knobbe, Martens, Olson & Bear, LLP

(57) ABSTRACT

A method of assessing the state of the lining of the small intestine in a mammal or human injesting a suitable labelled test substrate which requires conversion by a brush border enzyme for transport across the small intestinal lining. Suitable substrates include sucrose and maltose. The transport of these can very conveniently be measured by assessing the amount of label present in carbon dioxide expelled in the breath after a period of time. It has been shown that this method has application to assessing damage cause by chemotherapeutic induced mucositis as well as gastroenteritis with an infectious cause.

18 Claims, 8 Drawing Sheets

OTHER PUBLICATIONS

Klein, et al., "Applications of Stable Isotopes to Pediatric Nutrition and Gastroenterology: Measurement of Nutrient Absorption and Digestion Using 13C", J. of Pediatr. Gastroenterology and Nutrition, 4:9-19 (1985).

Lo, et al., "Breath Tests: Principles, Problems, and Promise", Adv. Pediatr., 29:105-127 (1982).

Hoekstra, et al., "Evaluation of 13CO2 Breath Tests for the Detection of Fructose Malabsorption", J. Lab. Clin. Med., 127(3): 303-309 (1996).

Hiele, et al., "Measurement of the Rate of Assimilation of Oligo- and Polysaccharides by 13CO2 Breath Tests and Isotope Ratio Mass Spectrometry", Biomed. and Environmental Mass Spectrometry, 16:133-135 (1998).

Koetse, et al., "Non-Invasive Detection of Low-Intestinal Lactase Activity in Children by Use of a Combined 13CO2/H2 Breath Test", Scandinavian J. Gastroenterol., pp. 35-40.

King, et al., "the Use of Breath Tests in the Study of Malabsorption", Clinics in Gastroenterology, 12(2):591-610 (1983).

Sasaki, et al., "intestine: Physiological Function Test and Inflammation—Evaluation of Intestinal Mucosal Function by Measuring Expired 14CO2 After oral Administration of 14C-Putrescine", Journal of Gastroenterology and Hepatology, 16:986-990.

* cited by examiner (a) Control jejunum (b) Methotrexate-treated jejunum

BREATH TEST

FIELD OF THE INVENTION

This invention relates to a diagnostic test to assess the state of the small intestine, and more particularly to the use of a breath test to do so.

BACKGROUND TO THE INVENTION

The lining of the small intestine plays a particularly important role in the health and well being of an individual. It represents the major interface for nutrient uptake in the human body. The majority of energy uptake is through the brush border lining the small intestine. The surface area of the brush border is maximised by structures known as villi that protrude into the gut lumen.

Serious health ramifications can result should the functioning surface area of the brush border be significantly reduced, for example, by reason of the elaboration of the villi being reduced or by reason of damage to the enterocytes lining the brush border.

Damage to the small intestinal tract can be occasioned in any number of ways. For example, damage may result from an infection by a pathogen, or by conditions such as Crohn's disease, Coeliac disease and Diabetes. Alternatively, various treatments might occasion damage, for example, by the use of bactericides such as certain antibiotics or more usually by the application of anticancer treatments the enterocytes being particularly prone to the latter two as a result of their rapidly dividing nature.

The degree of enterocyte damage can be modulated for any of the above conditions, for example, by altering the severity of the treatment undertaken or by administering palliative agents. Such remedial action is currently not taken until manifestation of physiological symptoms resulting from an impairment of the brush border. Given that in many cases the subjects concerned are already under considerable stress it is highly desirable to address such potential failure as early as possible more particularly before the onset of such a failure. This therefore requires a suitable diagnostic method that might be predictive of such failure.

Currently the method used for definitive diagnosis of small intestinal damage and dysfunction is by biochemical and histological analysis of small bowel biopsy. The major disadvantages of this approach are (a) the invasiveness of taking a biopsy and (b) the extrapolation of information on enzyme activity and damage to the intestine from a small sample site to the entire small intestine. The latter assumes that conditions affecting the small intestine produce a uniform response throughout, however it is known that many conditions are focal in nature. This method is simply impractical to perform on a repeated basis.

Breath hydrogen tests are taken as a measure of small intestine malabsorption, and are an alternate approach to assessing damage to the small intestine. Breath hydrogen results from fermentable material being malabsorbed in the small intestine and presented to the colon for fermentation by microflora present in the large intestine. Thus reduction in the surface area of the small intestine or loss of enzyme activity will result in passage of digestible sugars (for example sucrose) to the colon and subsequent $H_2$ production indicating problems with the small intestine. However the test is only appropriate if hydrogen-producing bacteria are present in the colon. It is thought that there is a significant proportion of human and animal populations (estimated at up to 20%) that do not have hydrogen producing bacteria resident in the large intestine. This then creates the potential for false negatives. In addition such tests are qualitative only and therefore do not give an estimate of the degree of damage or dysfunction that is present. These are major limitations of the clinical usefulness of the breath hydrogen test.

A third test that allows an assessment of the integrity of the small intestine is the sugar absorption test (SAT). The SAT measures the appearance of certain sugars in the urine (e.g. lactulose, rhamnose and sucrose). These are indicative of a damaged small intestine lining. SAT's are currently used in a limited fashion to assess intestinal permeability as a measure of the integrity of the small intestinal lining. Although these tests offer the advantage of being non-invasive they only test for one specific component of the small intestinal structure and function, that being the ability to maintain an impermeable barrier separating the contents of the gastrointestinal tract from the systemic system. The main disadvantages of SAT's are (a) the low diagnostic specificity (b) difficulty in performing the tests in the young, and (c) analysis of urinary excretions of the ingested probes involves intricate multi-step protocols which are difficult to perform.

SUMMARY OF THE INVENTION

In one specific form the present invention might be said to relate to a method of assessing the physical state of the lining of the small intestine in an animal or human,
    preferably allowing a period of fasting of the animal or human,
    taking an initial breath sample,
    administering an acceptably labelled test substrate of an indicator enzyme, the indicator enzyme being specifically expressed on the brush border of enterocytes lining the small intestine,
    the indicator enzyme being one that is constitutively expressed and present in substantially all of the members of the population of the animal or human,
    taking one or more further breath samples after administering the labelled test substrate,
    ascertaining the level of a labelled carbon dioxide in the breath samples, and
    calculating the change in labelled carbon dioxide after ingestion of the test substrate.

The indicator enzyme is preferably a dissacharidase and might particularly be a sucrase which is constitutive and is expressed on the enterocytes of all normal individuals. The test substrate for this is labelled sucrose. A further indicator enzyme the presence of which can be assayed to give an indication of the above defect is a maltase. The test substrate for this is labelled maltose. There is a very small proportion (0.2%) of the human population that has a deficiency known as sucrose-isomaltase deficiency where this form of the invention cannot be used, although it can be used to detected this condition. Additionally unlike, for example, lactose the two indicator enzymes referred to above do not have a dramatic cut off of activity in a subpopulation, that is non-caucasian. An additional aspect of the indicator enzyme is that activity is exposed substantially only in the small intestine, which therefore has the advantage of assessing specifically the integrity or activity in the small intestine. It will be understood that the invention may not necessarily be limited to assaying for activity of the two dissacharidases referred to above, it might also relate to other indicator enzymes with the same characteristics referred to above. However the present invention has very specifically shown that sucrose is able to be used for this purpose and is reliable for doing so. It is postulated that at least maltose should also be reliable for that purpose.

In another broad form the invention might be said to reside in a method of assessing the state of the lining of the small intestine in a animal or human, taking an initial breath sample, administering an acceptably labelled test substrate, the test substrate being selected from the group consisting of sucrose and maltose, taking one or more further breath samples after administering the labelled test substrate, ascertaining the level of a labelled carbon dioxide in the breath samples, and calculating the change in labelled carbon dioxide after ingestion of the test substrate, and comparing the change to a standard to make the assessment.

One or more atoms of the test substrate may be labelled so that carbon dioxide ($CO_2$) is formed to include these labelled atoms. It will thus be readily apparent that the labelled atom might be either a carbon or an oxygen. A number of known labels might be used. A most convenient label might be the use of an isotope other than the most common isotopes, the most common isotopes being $^{12}C$ and $^{16}O$. Preferably, because the substrate is to be ingested, the isotope used is one that emits a low energy or no radiation, and most preferably none, for that reasons $^{13}C$ is a preferred choice. $^{13}C$ is a stable isotope, and is present in sucrose produced in certain plants at sufficiently high levels to not require addition of synthetically produced $^{13}C$-sucrose. Where other enzymes are to be measured and $^{13}C$ maltose or other substrate is to be measured it will be understood that the labelled isotope might need to be made synthetically. Additionally to elicit a stronger signal some synthetic sucrose may be added to the naturally enriched sucrose.

Other isotopes that might be used include $^{14}C$. $^{14}C$ is used in other breath test analyses and is considered generally safe for many individuals, it is not used generally on young children and women of child bearing age. Another common form of radioisotope used is $^{18}O$.

It will be understood as with other uses of labelled compound the extent of labelling need only be measurably different to that which occurs naturally. With $^{13}C$-sucrose the abundance in, for example, cane sugar is about 11-12 atom $^o/_{oo}$, and a measurable result is achievable after ingestion of a reasonable quantity of sucrose. Should the specific activity of the sucrose be higher, then less may need to be ingested. The specific activity required can, of course, be modulated to empirically find a level that provides a convenient result.

Other forms of labelling of atoms might also be used and this invention might encompass such labelling.

Preferably the animal or human to be tested fasts for a period of time before ingestion of the labelled substrate. This may be an overnight fast of perhaps 8 hours, or an alternative period of time perhaps 2 or 3 hours. The purpose of the fasting is to bring a degree of consistency to the test, to ensure, for example, that material that has otherwise been ingested does not compete with the test substrate for the enzyme activity, or alternatively there may be other factors that interfere significantly with the test, for example, induction of other enzymes that might compete with the indicator enzyme for the test substrate.

A breath sample is taken before the test substrate is administered. This is to ascertain a base level of labelled to unlabelled $CO_2$ for example, $^{13}CO_2$ to $^{12}CO_2$. This is then used to compare variation after the test substrate has been administered. There will be, by reason of natural background, a level of, for example, $^{13}CO_2$ present on the breath of the mammal or human. The method of the present invention will thus measure increases above that level. It might however be possible that no control breath sample needs to be taken and the one or more breath samples taken after ingestion of the test substrate might be tested as against a suitable absolute level of $^{13}CO_2$ indicative of damage.

The breath sample can be taken by any known method, and that could be as simple as blowing into a container, a glass tube or an inflatable bag. Where the sample is to be taken by an animal, more complex arrangements might be required. It will be understood that collection will usually entail avoiding collection of air from the dead space and thus for humans the first approximately 150 ml will normally not be collected.

The sample will then be tested for the relative quantity of labelled $CO_2$ in the breath. The procedure used for testing these may be any one suitable for testing the amount of labelled material compared to unlabelled material.

It is desired to provide for an internal standard to measure against the labelled $CO_2$. In a very convenient form the internal standard might be to also measure the unlabelled $CO_2$. Thus for $^{13}CO_2$ an isotope ratio mass spectrometer may be used to measure the ratio of $^{13}CO_2$ to $^{12}CO_2$ and any changes in that ratio will be noted.

The time over which damage can be detected has been checked empirically and significant divergence has been found from about 45 minutes after ingestion through to about two to three hours after ingestion of a solution of sucrose. The time of sampling might depend on a range of conditions including the state in which the test substrate is given.

It is found that there is a response with an increase in labelled $CO_2$ no matter whether the test animal or human has a damaged small intestinal lining, and thus use of a control, or comparison with another standard is highly desirable. It is anticipated that a threshold level of the indicator enzyme activity as measured by the $CO_2$ will be empirically ascertained to indicate when remedial action is required. Adjustment may need to be made to the calculation of threshold to take into account the age or weight of the subject or the condition that the subject suffers from.

For a better understanding the invention will be described by reference a number of examples and drawings.

* indicates significant difference in sucrase activity within control group (p<0.05)

** indicates significant difference in sucrase activity between control and methotrexate-treated rats (p<0.0005).

Figure 4:
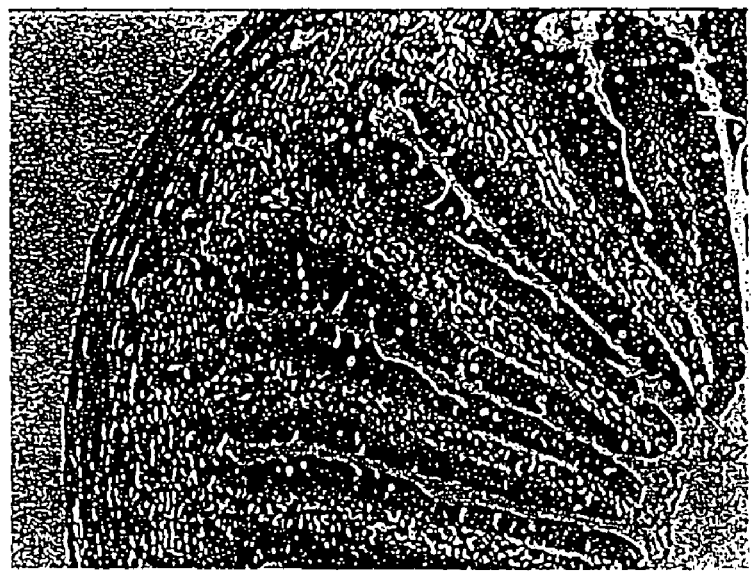
Figure 4:
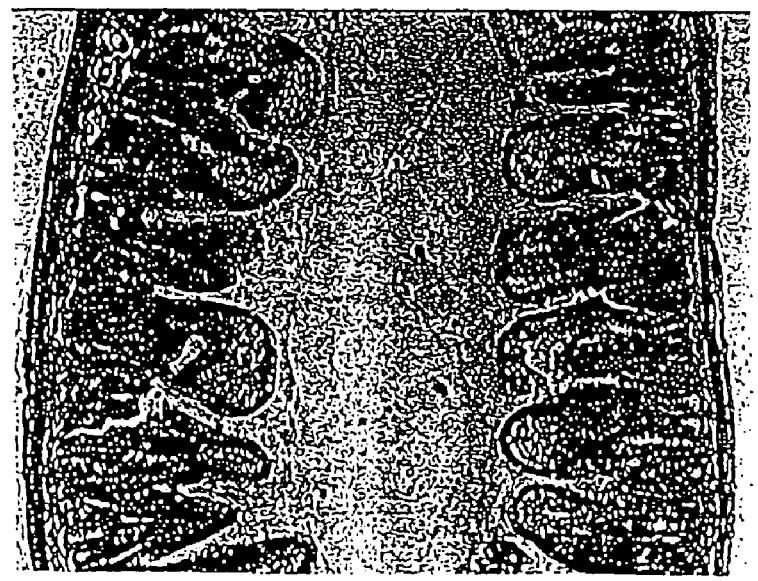

FIG. 4 are representative transverse sections of jejunum stained with haematoxylin and eosin from a control rat (a) and a rat treated with methotrexate seven days earlier (b), 10× magnification. Villi are visibly shorter and stubbier in the methotrexate-treated jejunum.

Figure 5:
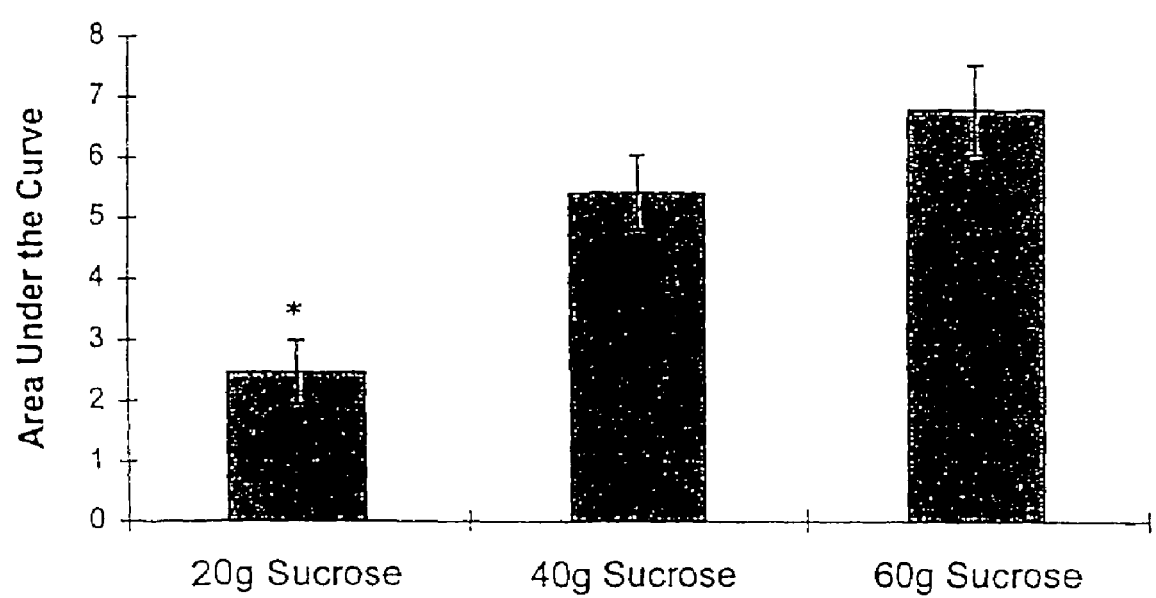

FIG. 5. Breath $^{13}CO_2$ levels in healthy humans in response to the ingestion of 20 g, 40 g and 60 g $^{13}C$-sucrose (n=10). Values are expressed as the area under the curve and presented as mean±SEM.

* indicates significant difference in AUC from 40 g sucrose and 60 g sucrose.

Figure 6:
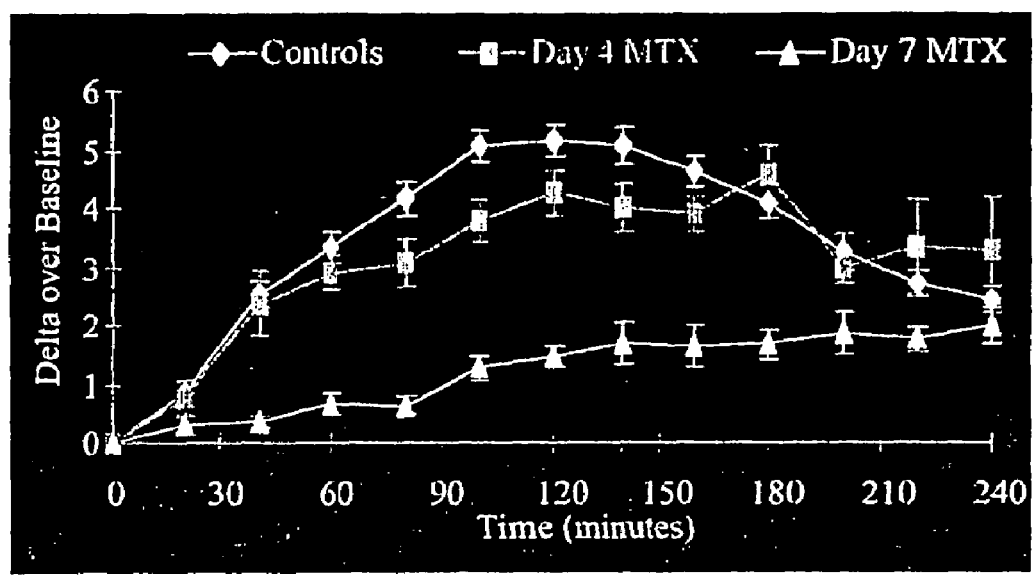

FIG. 6 is a graph of breath $^{13}CO_2$ levels in rats 4 day (squares) or 7 days (triangles) following treatment with methotrexate, and a control (diamonds).

Figure 7:
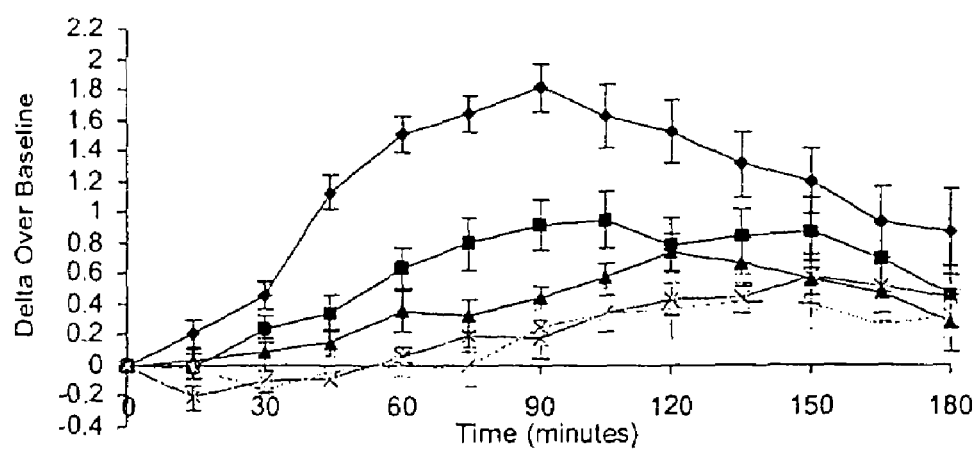

FIG. 7 is a graph of breath $^{13}CO_2$ levels in human volunteers that have ingested four different levels of acarbose in addition to $^{13}C$-sucrose. Diamonds represent 20 g sucrose (no inhibitor, n=10), Squares are 20 g sucrose with 25 mg acarbose (n=9), triangles represent 20 g sucrose with 50 mg acarbose (n-9), crosses represents 20 g sucrose with 100 mg acarbose (n-8) and stars represent 20 g sucrose with 200 mg acarbose (n=9)

Figure 8:
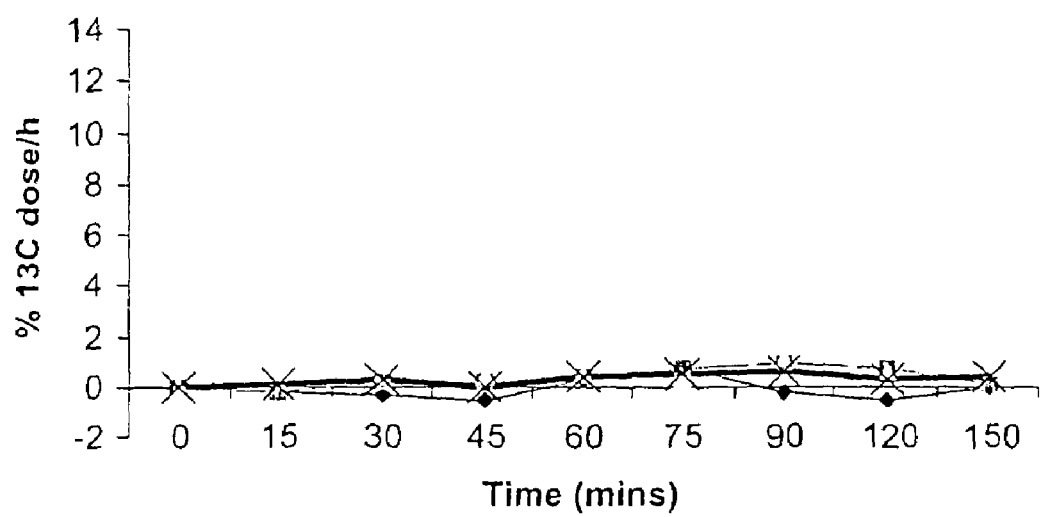

FIG. 8 is a graph showing the percentage $^{13}CO_2$ expired during the sucrose breath test in three aboriginal children with gastroenteritis, the mean is represented as crossed and the thickened line.

Figure 9:
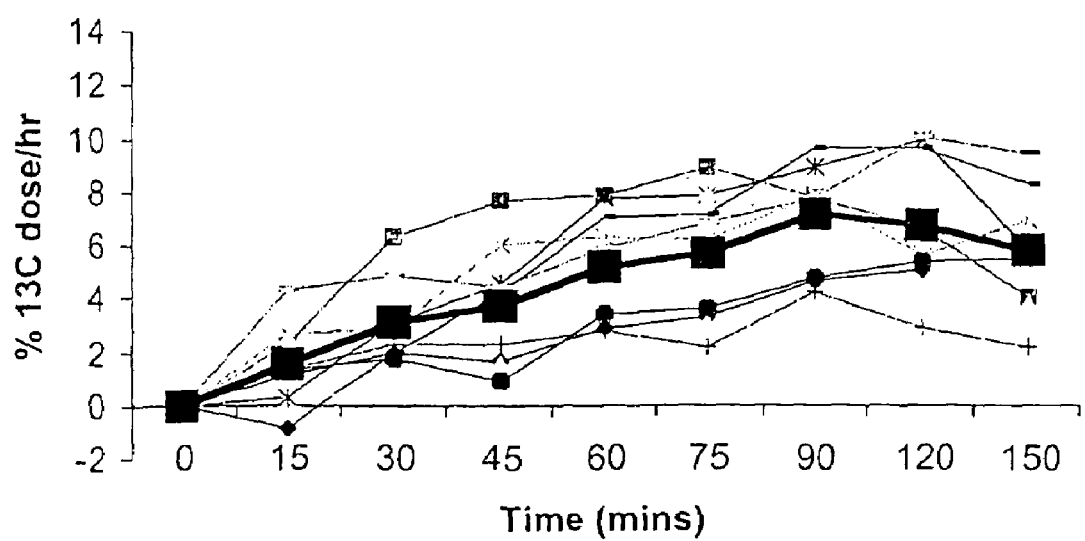

FIG. 9 is a graph shows the same parameter as in FIG. 8 in a group of 10 healthy aboriginal children, the means is represented by the thickened line with squares.

Figure 10:
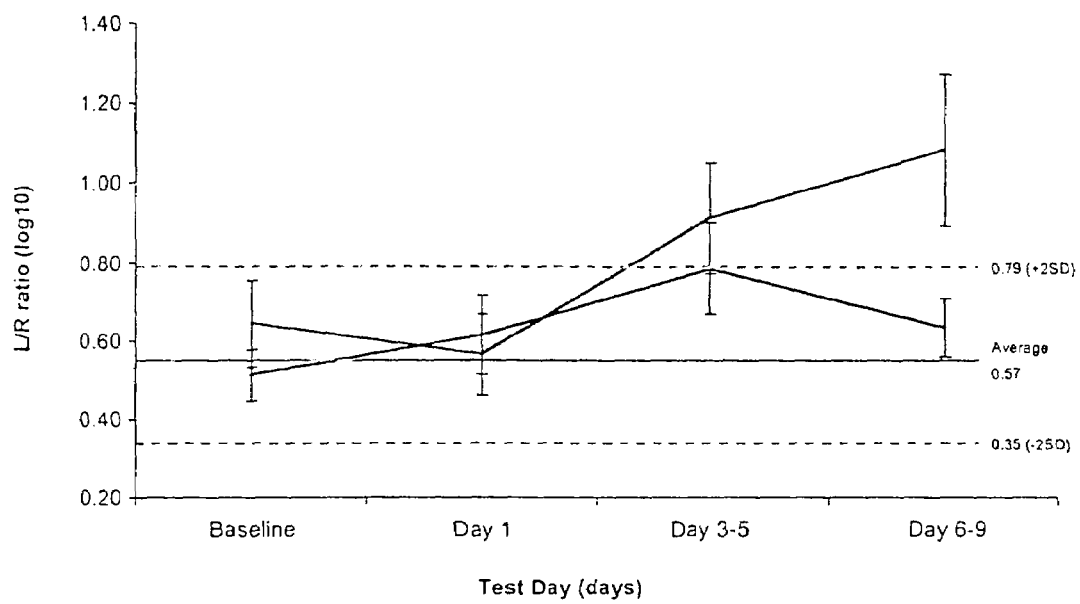

FIG. 10 Time course of small intestinal barrier function (SIP), represented by L/R permeability ratio, between No Mucositis group (n=8)(darker line) and Mucositis group (n=6)(lighter line). On test day 6-9 Mucositis group n=4. The control mean±2SD are shown as the solid and broken horizontal green lines. Data expressed as mean±SEM. Significance denoted by * ($p<0.05$).

Figure 11:
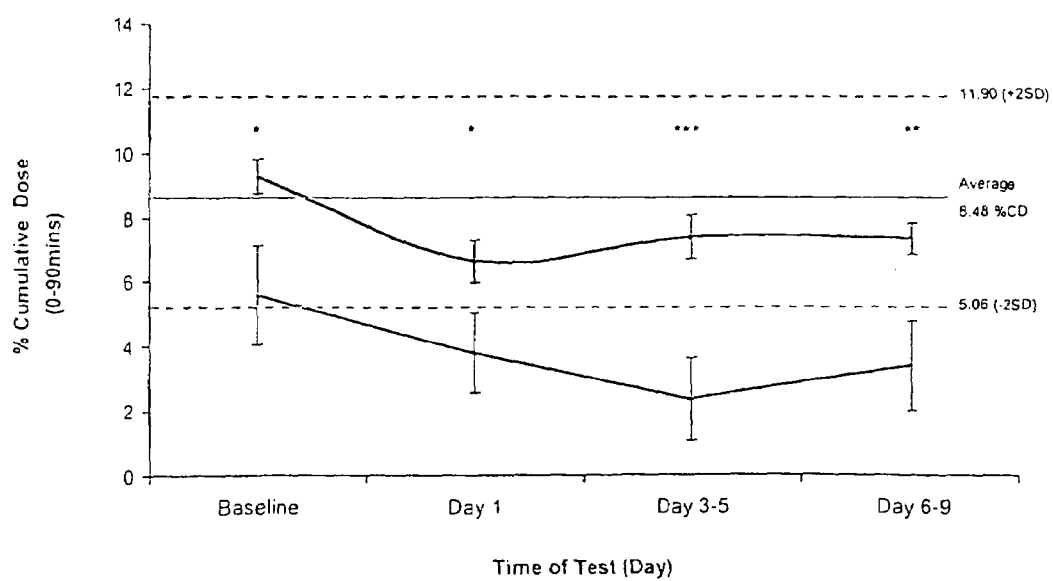

FIG. 11 Time course of small intestinal absorptive capacity, represented by % CD 0-90 min, between no mucositis group (n=8)(darker line) and mucositis group (n=6)(lighter line). On test day 6-9 Mucositis group n=4. The control mean±2SD are shown as the solid and broken horizontal green lines. Data expressed as mean±SEM. Significance denoted by * $p<0.05$,  $p<0.005$ and * $p<0.001$.

Figure 12:
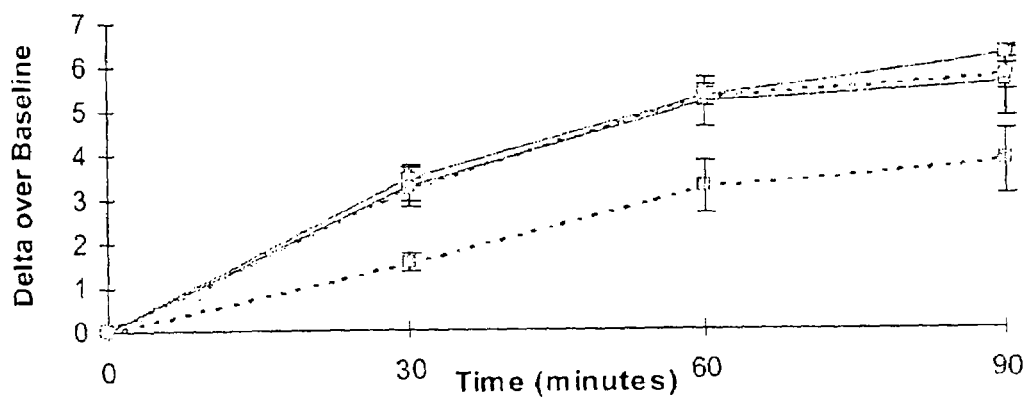

FIG. 12 Effects of folinate on the breath $^{13}CO_2$ levels following sucrose gavage in rats 52 hrs after MTX treatment (mean±SEM )(n=4/group). The filled squares represent 52 hour folinate, the filled circles 52 hours folinate. The open squares represent Pre-MTX no folinate, the open circles represent Pre-MTX folinate.

Figure 13:
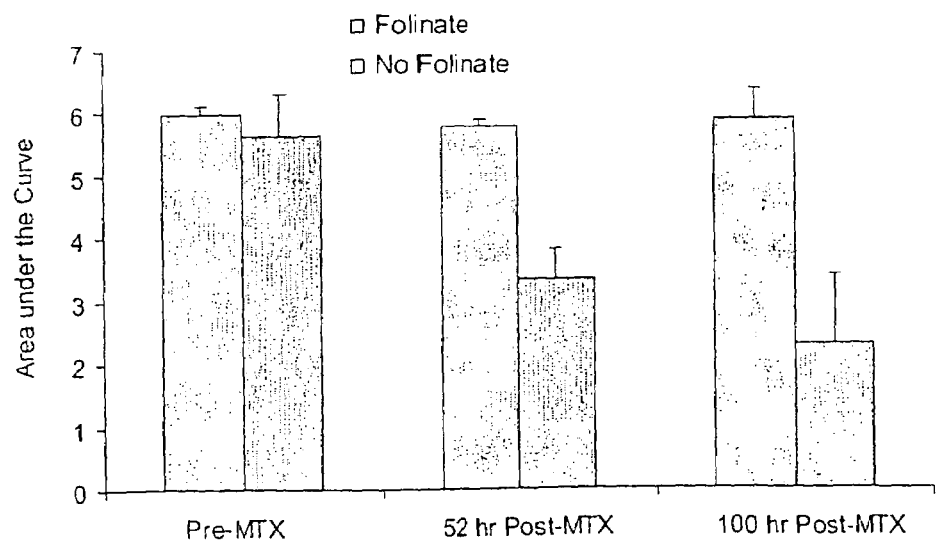

FIG. 13 Effects of folinate on the breath $^{13}CO_2$ levels following sucrose gavage in rats 52 hrs after MTX treatment (mean±SEM)(n=4/group). The first of the pairs of bars represents folinate, the second no folinate.

Figure 14:
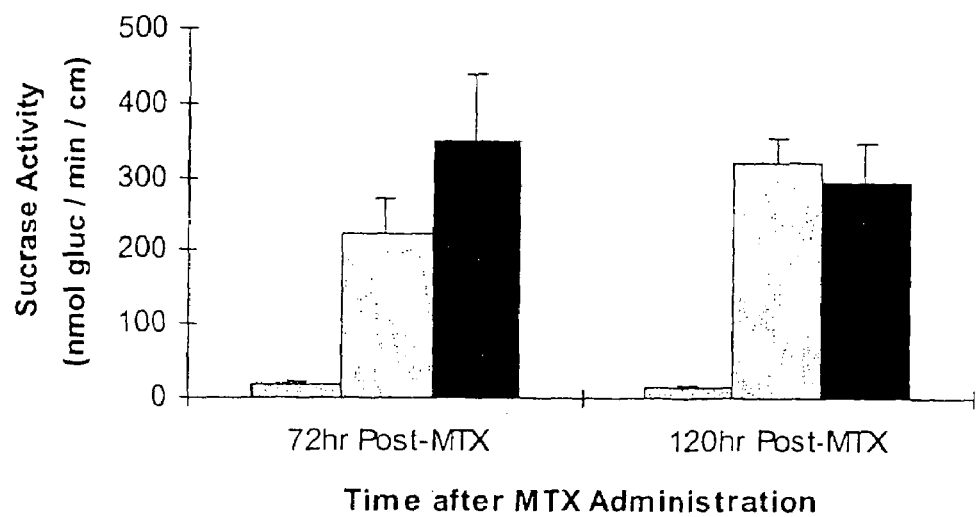

FIG. 14 Effects of folinate on jejunal sucrase levels of rats 72 and 120 hours post MTX-treatment (mean±SEM, n=4, except 2 in control groups). The first of the triplets of bars represent MTX, the second MTX and folinate and the third a control with no MTX.

Figure 15:
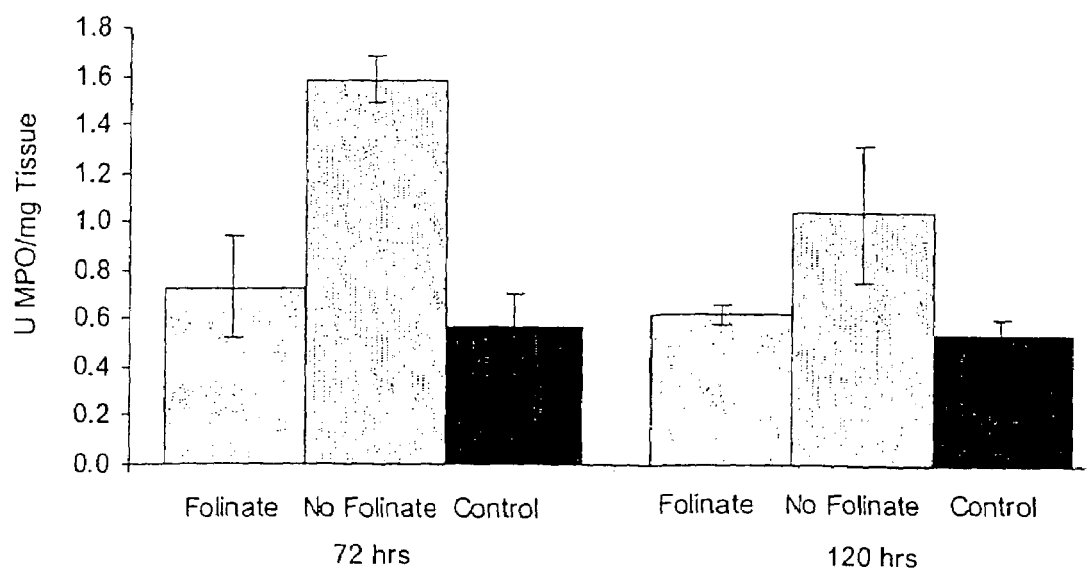

FIG. 15 Effects of folinate on jejunal MPO levels in rats 72 and 120 hours post MTX-treatment (mean±SEM, n=4, except 2 in control groups). The first of the triplet of bars represents MTX and folinate, the second MTX and no folinate and the third the control.

DETAILED DESCRIPTION OF THE INVENTION

EXAMPLE 1

The Methotrexate Model of Gastrointestinal Disease in Rats

Material and Methods

Animals

Sixteen adult male Sprague Dawley rats were individually housed in Techniplast metabolism cages with an environmental temperature of 25° C. and a 12-hour light:dark cycle for the duration of the study. Eight rats (mean weight 182.4±2.8 g) were treated with a 2.5 mg/kg subcutaneous injection of methotrexate (Lederle Laboratories, Baulkham Hills, NSW, Australia) in 0.9% sodium chloride on three consecutive mornings (i.e. day 1, 2 and 3 of the protocol). Rats were fed an 18% Casein diet and allowed water ad libitum for the duration of the seven day protocol. The remaining eight rats (mean weight 211.3±4.8 g) were weight-matched to the methotrexate-treated rats from heaviest to lightest, and fed the same amount of 18% Casein diet ingested by their methotrexate-treated counterpart on each day of the seven day protocol.

The $^{13}C$-Sucrose Breath Test

Figure 1:
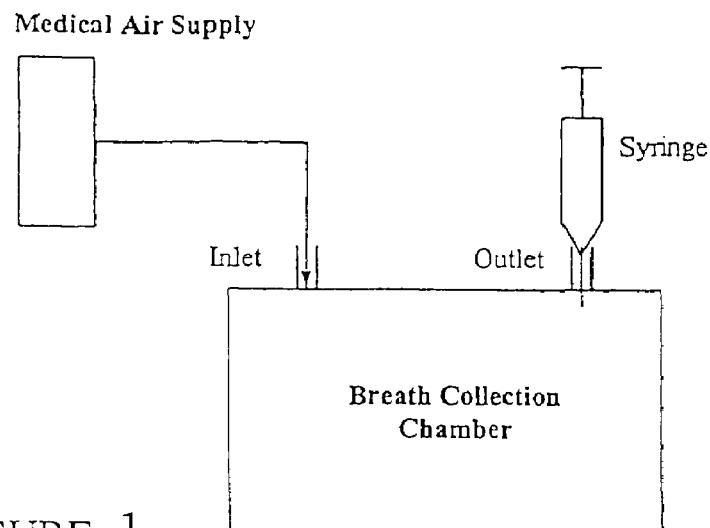
FIG. 1 is a diagrammatic description of the breath collection apparatus used in the first example, FIG. 2 breath $^{13}CO_2$ levels at 20-minute time points over 240 minutes following ingestion of a 2 ml $^{13}C$-sucrose solution in control rats (n=8) and rats treated with methotrexate 7 days earlier (n=8). Values are expressed as the change in breath $^{13}CO_2$ (delta) from baseline and presented as mean±SEM.

The $^{13}C$-Sucrose Breath Test was performed on all rats from 8 am on day 7 of the protocol. Rats were placed in the custom-built breath collection chamber (1 liter Pyrex container; FIG. 1) 10 minutes prior to sample collection. The chamber was closed after eight minutes and medical air was supplied to the chamber through the inlet for the remaining two minutes. Airflow was sufficient to flush the chamber of $CO_2$ in this two-minute period. At breath sample collection, the two-way taps fitted to the inlet and outlet were closed for two minutes, allowing the $CO_2$ exhaled by the rats to accumulate.

Breath samples were syringed (20 ml plastic; Becton Dickinson, Sandy, Utah, USA) from the outlet at the end of this two-minute period and medical airflow was immediately returned to the chamber. Breath samples were transferred via the syringe to a 10 ml evacuated glass tube (Exetainer, Labco Limited, High Wycombe, England) for $^{13}CO_2$ analysis. Each breath test was preceded by an overnight fast (13 hours) and a 15-minute acclimatisation period in the breath collection chamber. Following the collection of three baseline breath samples, rats ingested a 2 ml sucrose solution (AnalaR, BDH, MERCK Pty Ltd, Victoria, Australia; fixed dose 1 g/ml water) via orogastric gavaging. Breath samples were collected at 20 minute intervals for the following 240 minutes.

Kill Procedure and Tissue Collection

Rats were sacrificed in the afternoon of day 7 by cervical dislocation under $CO_2$ anaesthesia. The abdomen was opened via a midline incision and the liver and gut excised. The gut contents were flushed thoroughly with phosphate buffered saline, pH 6.0. The small intestine was placed on an ice-cold slab and divided into three sections: the duodenum comprising the intestine from the gastro-duodenal junction to the ligament of Treitz; the remaining intestine from the ligament of Treitz to the caecum was divided in half to provide jejunum and ileum of equal length. A 4 cm portion was excised from each intestinal section and was rapidly frozen in liquid nitrogen, before being transferred to a −70° C. freezer until determination of sucrase activity. A further 1 cm of each section was excised and fixed in methacarn fixative for two hours, transferred to 70% ethanol for 48 hours, and embedded in paraffin wax for histological analysis (Howarth et al., (1996).

In Vitro Assay of Sucrase Activity

Tissue from the duodenum, jejunum and ileum was prepared for the assay of sucrase activity according to the first two steps in the method of Shirazi and Beechley (1991). Briefly, the brush border membrane containing the disaccharidase enzymes was isolated via hypoosmolar shock followed by centrifugation. Three×1 ml aliquots of enzyme preparation were obtained from the duodenum, jejunum and ileum of each rat. Aliquots were stored in liquid nitrogen prior to being thawed and assayed for sucrase activity by the method of Dahlqvist (1968). This assay involves the addition of a known amount of sucrose (substrate) to the enzyme preparation for 30 minutes and the use of glucose oxidase to determine the amount of glucose liberated during this period. Enzyme activity was then related to the protein concentration of the enzyme preparation as determined by the method of Bradford (1976), in which a standard curve of bovine serum albumin concentration is used to ascertain the protein content of the sample. As a result, the sucrase activity representative of duodenal, jejunal and ileal brush border membrane was determined as $\mu$ mol of substrate hydrolysed at 37° C. at pH 6.0/mg protein/hour.

Histology

Tissue samples in paraffin wax were sectioned transversely at 21 $\mu$m, stained with haematoxylin and eosin to expose the structure of the intestinal mucosa, and examined by an under a light microscope (Howarth et al., 1996). A semi-quantitative histological assessment of intestinal damage was utilised to obtain an overall score of damage severity in the three sections of the small intestine. A severity score ranging from 0-3 was allocated for 11 histological features (table 1), such that the maximum severity score (33) indicated the most severe damage (Howarth et al., 1996).

TABLE 1

Histological parameters used to derive severity scores for methotrexate-induced intestinal damage.

| Intestinal wall component | Histological parameter |
| --- | --- |
| Mucosa | Villus fusion and stunting |
|  | Enterocyte disruption |
|  | Reduction in goblet cell numbers |
|  | Reduction in mitotic figures |
|  | Crypt disruption |
|  | Crypt cell disruption |
|  | Crypt abscess formation |
|  | Lymphocyte and Neutrophil infiltration |
|  | Capillary and lymphatic dilatation |
| Submucosa | Thickening/oedema |
| *Muscularis externa* | Thickening |

Data Analyses

Significance in all statistical tests was set at p<0.05.

Breath $^{13}CO_2$ Analyses

Breath samples were analysed for $^{13}CO_2$ by an isotope ratio mass spectrometer (IRMS; Europa Scientific, ABCA 20/20, Crewe, United Kingdom) equipped with a V410 data collection system. Isotope ratio mass spectrometric analysis of breath samples expresses results as a delta value, representing the ratio of $^{13}C/^{12}C$ in the sample in parts per thousand relative to the calcium carbonate international primary standard, Pee-Dee Belemnite limestone (South Carolina, USA)(Renes et al., (1997). Baseline levels of breath $^{13}CO_2$ were determined by averaging the delta of breath samples collected prior to the ingestion of sucrose. Results from the $^{13}C$-Sucrose Breath Test were then calculated as the change in breath $^{13}CO_2$ levels from baseline (i.e. delta over baseline: DOB) for each time point of breath collection over the period of interval sampling. The area under the "change in breath $^{13}CO_2$ level over time" curve (AUC) was calculated using the trapezoidal rule:

$$AUC = \Sigma[(DOB_{t1} + DOB_{t2})/2] \times (t2 - t1)$$

AUC data are presented as mean±SEM.

Significant differences between the AUC of controls and methotrexate treated rats was determined by an unpaired t-test.

In Vitro Sucrose Activity

Sucrase activity was expressed as specific activity relative to protein ($\mu$mol substrate hydrolysed at 37° C. at pH 6.0/mg protein/hour) and presented as mean±SEM. Sucrase activity from the three sections of intestine within either the control group or the methotrexate-treated group were compared using one-way analysis of variance and a Bonferroni post-hoc test. Significant difference in sucrase activity in the duodenum, jejunum and ileum of methotrexate-treated compared to control rats was detected using an unpaired t-test.

Histology

Histological severity scores were calculated and presented as median and range. The unpaired non-parametric Mann-Whitney two-sample test was employed to compare the severity scores of the methotrexate-treated rats with controls for each section of intestine.

Relationship Between Breath $^{13}CO_2$ and In Vitro Sucrase Activity

Pearson's Product-Moment Correlation was utilised to explore the relationship between breath $^{13}CO_2$ levels (AUC) and the in vitro sucrase activity of individual sections of small intestine (i.e. duodenum, jejunum and ileum). In addition, breath $^{13}CO_2$ levels (AUC) were also correlated to the average sucrase activity of the whole small intestine, which was calculated by expressing the sucrase activity of the duodenum, jejunum and ileum proportional to the length of intestine that each section represents, and summing the three results.

Results

The $^{13}C$-Sucrose Breath Test

Figure 2:
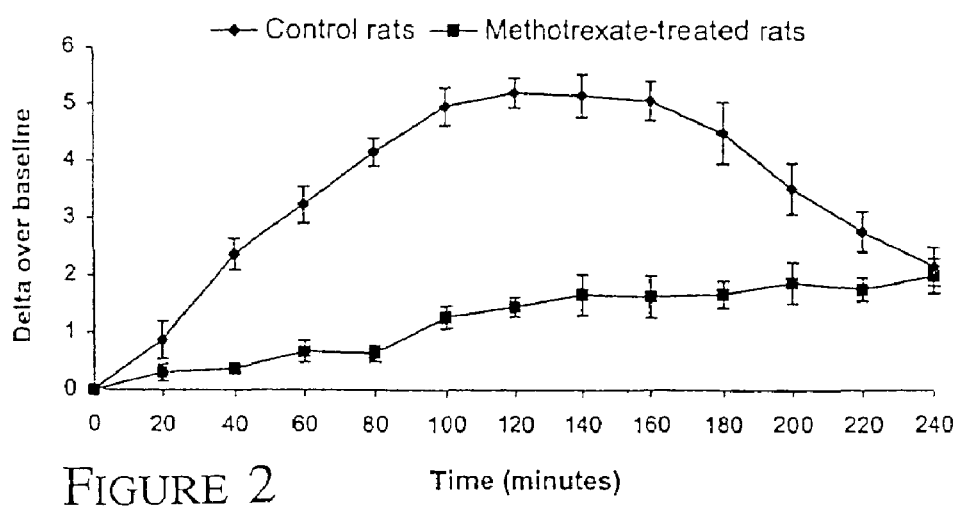

FIG. 2 compares the increase in breath $^{13}CO_2$ levels (DOB) occurring over the 240 minutes following sucrose ingestion in controls and methotrexate-treated rats on Day 7 of the protocol. The AUC observed in methotrexate-treated rats (AUC=4.7±0.56) was significantly lower than the AUC of controls rats (AUC=15.2±1.2; p<0.001).

In Vitro Assay of Sucrase Activity

Figure 3:
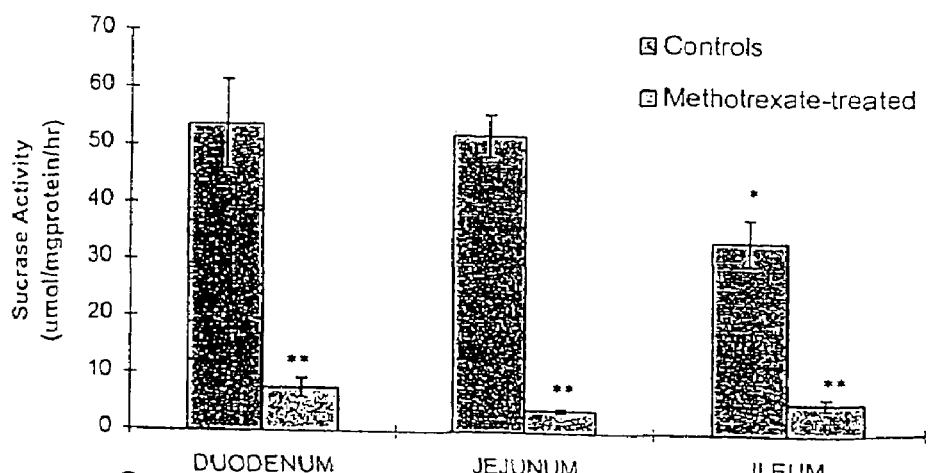
FIG. 3 sucrase activity (mmol substrate hydrolysed at 37° C. at pH 6.0/mg protein/hour) in the duodenum, jejunum and ileum of control rats (n=8) and rats treated with methotrexate seven days earlier (n=8). Data are presented as mean±SEM.

Sucrase activity (specific activity in $\mu$mol substrate hydrolysed at 37° C. at pH 6.0/mg protein/hour) was similar in the duodenum and jejunum and significantly lower in the ileum of control rats (p<0.05; FIG. 3). On Day 7 after methotrexate treatment, sucrase activity was significantly diminished in all three sections of intestine (p<0.0005). There was no significant difference in sucrase activity between the three sections of intestine in methotrexate-treated rats (p>0.05).

Histology

Methotrexate-treated rats exhibited significantly higher severity scores than control rats in all three sections of the small intestine (p<0.05)(Table 2). FIG. 4 illustrates an example of the effect of methotrexate on jejunal villus structure.

TABLE 2

Severity scores of small intestinal sections from control rats and rats treated with methotrexate seven days earlier.

|  | Control rats (n = 4) | Methotrexate-treated rats (n = 4) |
|---|---|---|
| Duodenum | 1.5 (0-3) | 8 * (4-11) |
| Jejunum | 2 (2-2) | 10 * (7-21) |
| Ileum | 1.5 (1-2) | 6.5 * (4-10) |

Values are the sum of scores for 11 independent histological criteria, whereby the severity of each parameter was scored from 0 to 3. Maximum severity score = 33: indicates greatest severity of damage. Data are presented as median (range).
* indicates significant difference from control severity score ($p < 0.05$).

Relationship Between Breath $^{13}CO_2$ and In Vitro Sucrase Activity

The sucrase activity of the duodenum, jejunum, ileum, and whole intestine (derived by pooling the data from all three sections) was correlated to the results of the $^{13}$C-Sucrose Breath Test (AUC)(Table 3). The strongest relationship between the level of sucrase activity in the small intestine and the level of breath $^{13}CO_2$ following sucrose ingestion was found using the representation of sucrase activity from the whole intestine.

TABLE 3

Correlation coefficient representing the relationship between small intestinal sucrase activity and breath $^{13}CO_2$ levels following the ingestion of naturally enriched sucrose in control and methotrexate-treated rats.

| Intestinal section | Correlation coefficient, r |
|---|---|
| Duodenum | 0.73 |
| Jejunum | 0.87 |
| Ileum | 0.88 |
| Whole Intestine | 0.92 |

A correlation coefficient of $r = \pm 1$ indicates a perfect linear relationship between the two.

Discussion

The digestion and absorption of a $^{13}$C-substrate by the small intestine and subsequent metabolism of the $^{13}$C-products in the liver leads to the production of $^{13}CO_2$ which can be measured in the breath (Koetse et al., 1999; Schoeller et al., 1980). An increase in breath $^{13}CO2$ relative to baseline levels reflects the digestion and absorption of the $^{13}$C-substrate by the small intestine (Koetse et al., 1999; Hiele et al., 1988; Maclean et al., 1983; Schoeller et al., 1980).

In this example, significantly lower levels of breath $^{13}CO_2$ were exhaled by methotrexate-treated rats compared to controls in the 240 minutes following ingestion of naturally enriched sucrose. These results indicate that the digestion and absorption of sucrose was significantly impaired following methotrexate-induced damage to the small intestine of rats.

Methotrexate, an inhibitor of DNA synthesis (Erdman et al., 1991), is known to cause extensive small intestinal mucosal injury in the rat (Vanderhoof et al., 1990; Howarth et al., 1996; Erdman et al., 1991). To determine whether the lower breath $^{13}CO_2$ levels observed in methotrexate-treated rats following the ingestion of sucrose were in fact related to a lower activity of sucrase, an in vitro assay of sucrase activity was performed on tissue from the duodenum, jejunum and ileum. The small intestine of rats treated seven days prior with methotrexate exhibited significantly reduced sucrase activity compared to control animals in all three sections of the intestine. Histological analysis of intestinal sections from control and methotrexate-treated rats revealed that methotrexate also induced significant structural damage in each of the sections examined. The detrimental effects of methotrexate on small intestinal structure and sucrase activity observed in this study are consistent with previous studies utilising the drug to induce injury to gastrointestinal mucosa Vanderhoof et al., 1990; Ruppin et al., 1988; Taminiau et al., 1980; Fiedorek et al., 1991; Renes et al., 1997; Verburg et al., 1997).

A strong, positive relationship was found to exist between the level of sucrase activity intrinsic to the rats' small intestine and breath $^{13}CO_2$ levels following the ingestion of sucrose. Significantly, this relationship was strongest when the in vitro sucrase assay data from control and methotrexate-treated rats were representative of the whole small intestine rather than the individual sections. In contrast to the results of small bowel biopsy, which in reality only measure local small intestinal parameters (Perman et al., 1978; Lembcke et al., 1989), the $^{13}$C-Sucrose Breath Test is a measure of the integrity of the entire small intestine.

EXAMPLE 2

Materials and Methods

Subjects

The study recruited 10 healthy, non-smoking adults (male n=2; female n=8) aged 19-37 years old (mean age 22+2 years) with mean weight 65.2+3 kg. Subjects had no known history of gastrointestinal or liver disease. Antibiotic and non-steroidal antiinflammatory drug use in the three weeks preceding the experiment and acute alcohol consumption the day preceding the experiment warranted exclusion.

Test Solutions

Subjects ingested 20 g, 40 g and 60 g sucrose (AnalaR, BDH, MERCK Pty Ltd, Victoria, Australia) dissolved in 100 ml water on separate occasions. The order of these breath tests was random for each subject. To determine whether the breath test was capable of detecting inhibition of sucrase activity, two volunteers ingested 2×100 mg sucrase inhibitor (Acarbose tablets, Glucobay™) crushed and dissolved in 30 ml water, immediately followed by 20 g sucrose dissolved in 70 ml water.

The $^{13}$C-Sucrose Breath Test

All subjects were required to fast for a minimum of eight hours prior to testing and for the three hour duration of the test period. Small amounts of water were permitted 30 minutes after ingestion of the test solution. Subjects provided two baseline breath samples immediately prior to ingestion of the test solution. Following ingestion of the test solution, breath samples were collected every 15 minutes for three hours. Physical activity was avoided during the three hour experimental period, particularly at breath collection time points. End-expiratory breath samples were provided by exhaling through a straw into 5×10 ml glass tubes (Exetainer, Labco Limited, High Wycombe, England). Three tubes were used for analysis of breath hydrogen content to detect malabsorption of the breath test substrate, the remaining two tubes were used for $^{13}CO_2$ analysis to determine sucrase activity.

One-way analysis of variance and a Bonferroni post-hoc test were applied to detect significant differences in AUC following the ingestion of the different test solutions.

Breath Hydrogen Analysis

Breath samples provided by human subjects were analysed for hydrogen content by gas chromatography (Quintron, Model DP Microlyzer, E.F. Brewer Company, Wisconsin). An increase in breath hydrogen >20 parts per million (ppm) above baseline levels was taken to indicate malabsorption of substrate and subsequent fermentation by resident colonic bacteria (Perman et al., 1978; Davidson et al., 1985).

Results

Dose-Response Relationship

The AUC over 180 minutes following sucrose ingestion was significantly increased when increasing the dose from 20 g to 40 g sucrose (p<0.01) and from 20 g to 60 g sucrose (p<0.001). AUC was not changed when the dose was increased from 40 g to 60 g sucrose (FIG. 5).

Effect of a Sucrase Inhibitor on the $^{13}$C-sucrose and Hydrogen Breath Tests

The breath $^{13}CO_2$ (AUC) and hydrogen (ppm) levels of two hydrogen-producing subjects who ingested 20 g sucrose with and without 200 mg sucrase inhibitor is reported in table 4. In the presence of the inhibitor, acarbose, AUC was diminished by 57% and 93% respectively, while breath hydrogen increased to a maximum of 68 ppm and 79 ppm respectively.

TABLE 4

Effects of a Sucrase Inhibitor on Breath $^{13}CO_2$ and Hydrogen levels in response to the ingestion of 20 g Sucrose.

| | Breath $^{13}CO_2$ (AUC) | | Breath Hydrogen (ppm) | |
|---|---|---|---|---|
| | Subject 1 | Subject 2 | Subject 1 | Subject 2 |
| 20 g Sucrose | 1.695 | 2.096 | 2 | 2 |
| 20 g Sucrose + 200 mg Acarbose | 0.106 | 0.891 | 79 | 68 |

Raw values are presented for each subject (n=2). Breath $^{13}CO_2$ is expressed as the area under the curve representing the increase in breath $^{13}CO_2$ over 180 minutes following the ingestion of the test solution. Breath hydrogen values represent the maximum change from baseline occurring over 180 minutes, expressed in parts per million (ppm). An increase in breath hydrogen >20 ppm indicates malabsorption of carbohydrate (Perman et al., 1978; Davidson et al., 1985).

Discussion

Breath $^{13}CO_2$ levels were significantly increased when the dose of $^{13}$C-sucrose ingested was increased from 20 g to 40 g and 20 g to 60 g but not for 40 to 60 g. Since the subjects were all healthy with no known gastrointestinal or liver disorders, complete digestion and absorption of the ingested sucrose was assumed. Therefore, these results suggest that increasing the amount of $^{13}$C-sucrose available to the sucrase enzyme, thereby increasing product formation, is reflected by increased breath $^{13}CO_2$ levels but an optimal level may be between 20 to 40 g.

Baseline variability in breath $^{13}CO_2$ levels can decrease the sensitivity of breath tests employing $^{13}$C-substrates (Klein and Klein, 1985). For this reason, the $^{13}$C-enrichment of the dose of sucrose must be sufficient to generate a measurable increase in breath $^{13}CO_2$ in all individuals (Stellaard et al., 1998). In this example, 20 g sucrose was sufficient to increase breath $^{13}CO_2$ levels relative to baseline in all subjects, where the increase in breath $^{13}CO_2$ levels (AUC) ranged from 0.4 to 5.6. This large inter-individual variability can be attributed to differences in baseline breath $^{13}CO_2$ levels between subjects Schoeller et al., 1980). The ingestion of 20 g naturally enriched sucrose by subjects with a high baseline did not considerably increase breath $^{13}CO_2$ levels. In contrast, a dose of 40 g naturally enriched sucrose doubled the amount of $^{13}$C label administered and increased breath $^{13}CO_2$ levels to a greater extent. A higher dose of sucrose is therefore able to reduce the de-sensitising influence of high baseline breath $^{13}CO_2$ levels (Ruppin et al., 1988). Another method of improving the sensitivity of the $^{13}$C-Sucrose Breath Test would be to administer a standardised diet comprising foods not naturally enriched with $^{13}$C for 3-5 days preceding the experiment (Ruppin et al., 1988). This would have the effect of lowering baseline breath $^{13}CO_2$ levels, such that a dose of naturally enriched sucrose as low as 20 g may be suitable to signal digestion and absorption of sucrose in all individuals.

Acarbose, the potent competitive inhibitor of sucrase employed in this study, is very similar in structure to sucrose (Hanozet et al., 1981) but, unlike sucrose, is neither degraded nor absorbed by the small intestine (Ruppin et al., 1988). When ingested in combination with sucrose, acarbose effectively decreases its digestion and absorption (Ruppin et al., 1988; Hanozet et al., 1981). In this study, administration of 200 mg acarbose immediately prior to the ingestion of 20 g sucrose resulted in a large increase in hydrogen production and a marked decrease in breath $^{13}CO_2$ levels. The increase in breath hydrogen in the presence of the inhibitor indicated that the malabsorbed sucrose entered the colon and was fermented by the resident bacterial flora (Perman et al., 1978; Davidson et al., 1985). The $^{13}$C-Sucrose Breath Test results appear to reflect the inhibition of sucrase, however they may be attributable to another factor limiting the digestion and absorption of sucrose. Acarbose has been shown to increase the flow rate of intestinal contents because sucrase inhibition results in the presence of excess osmotically active sucrose in the small intestinal lumen (Ruppin et al., 1988). A decrease in small intestinal transit time may contribute substantially to the marked reduction in breath $^{13}CO_2$ levels observed in this study (Koetse et al., 1999), due to the reduced contact with the intestinal brush border for digestion by sucrase.

EXAMPLE 3

Effect of Differing Temporal Regimens of Methotrexate on Rats

Three groups of rats (n-8) were treated as in Example 1 above with either no methotrexate, methotrexate for 4 days or methotrexate for seven days. The rats were breath tested as above at 15 minute intervals up to 240 minutes. The results of this can be seen in FIG. 6. There is a clear quantal difference in the degree to which the day 4 methotrexate treatment affect the sucrase activity, compared with day 7 methotrexate treatment.

EXAMPLE 4

Effects of Varying the Level of Acarbose on $^{13}CO_2$ Breath Test

The sucrose breath test was conducted on (n=10) healthy humans, using a range of concentrations of acarbose ingested together with the $^{13}$C-sucrose. The experimental procedure was the same as used in example 2. Time samples were taken at 15 minute intervals from the time of ingestion up to 180 mins. The results can be seen in FIG. 7.

It can thus be seen that the measure of $^{13}CO_2$ in breath is inversely proportional to the level of acarbose added up to about 100 mg acarbose. Acarbose is an inhibitor of the sucrase enzyme, and at the levels used in this experiment represent progressive inhibition of the sucrase enzyme.

This then shows that the $^{13}CO_2$ breath test can give a quantitative measure of the degree of inhibition.

EXAMPLE 5

Preliminary Data with Patients with Gastroenteritis and Gut Mucositis

The tests conducted were substantially as described for Example 2 above.

Gastroenteritis

FIG. 8 shows the percentage $^{13}CO_2$ expired during the sucrose breath test in three aboriginal children with gastroenteritis. FIG. 9 shows the same parameter in a group of 10 healthy aboriginal children. There is a clear discrimination between those with a damaged mucosa compared with the normals. The sick children show almost no signal over the 150 min testing period.

Gut Mucositis

Preliminary data for gut mucositis has shown marked depression in children with severe mucositis compared with those who experience few adverse symptoms.

TABLE 5

| Patient | SBT baseline (cumulative | SBT day 1 | Ratio (B/D) |
|---|---|---|---|
| ALL(PB) | 10.14 | 5.41 | 2 |
| ALL(GR cycle 2) | 4.35 | 0.53 | 8 |
| ALL(AT) | 9.13 | 5.66 | 1.6 |
| ALL (GR cycle 1) | 9.12 | 7.68 | 1.2 |
| Neuroblastoma (EM) | 5.69 | 0.57 (d4) | 10 |

The patients with a ratio of baseline:during (B/D) below 2 showed little or no symptoms of mucositis. Those with a higher ratio experienced more severe symptoms with the patient showing a B/D of 10 being admitted to intensive care with dehydration and severe mucositis.

EXAMPLE 6

Sucrose Breath Test as a Marker for Mucositis

Methods and Materials

Subjects

All subjects had no known history of gastrointestinal or liver disease and were non-diabetic. 26 healthy, children (male n=11, female n=16) aged 5-17 years old (11.2±0.8 yr, mean±SEM), with a height and weight of 150.7±3.7 cm and 45.4±3.2 kg, respectively, were recruited for the study (Table 6). Control subjects refrained from ingestion of antibiotics, antihistamines and non-steriodal anti-inflammatory drugs four weeks prior to testing.

26 cancer patients were approached for the study at the Women's and Children's Hospital, Adelaide, Australia, from April 2001 to April 2002. 13 patients declined to join the study and 13 patients (male n=7, female n=6) receiving HD-chemotherapy were recruited. Of the 13 patients enrolled, three withdrew due to patient/parent request, one was withdrawn due to noncompliance and one withdrew due to interstate relocation. The characteristics of the 8 remaining patients enrolled in the study are given in Table 6, and their chemotherapy regimen for cycle 1 and/or cycle 2 testing are given in Table 7. All patients had received numerous cycles of chemotherapy prior to enrollment (non-naive). Patients were aged 5-16 years (10.4±1.0 yr, mean±SEM) with a height and weight of 143.3±8.9 cm and 38.8±6.9 kg, respectively (Table 6).

Informed written consent was obtained from all subjects and ethical clearance was granted from the Research Ethics Committee of the Women's and Children's Hospital, Adelaide, Australia. The study was carried out in accordance with the Declaration of Helsinki.

TABLE 6

Characteristics of the controls (n = 26) and patients (n = 8). Showing the number of cycles of chemotherapy assessed (n = 14) with respect to cancer diagnosis.

| Subjects | | |
|---|---|---|
| | Controls | |
| Male | | n = 11 |
| Female | | n = 16 |
| Age (years) | | 11.2 ± 0.8 |
| (range) | | (5-17) |
| Height (cm) | | 150.7 ± 3.7 |
| Weight (kg) | | 45.4 ± 3.2 |
| | | Cycles Tested |
| | Patients | |
| Male | | 5 (3 patients) |
| Female | | 9 (5 patients) |
| Age (years) | | 10.4 ± 1.0 |
| (range) | | (5-16) |
| Height (cm) | | 143.3 ± 8.9 |
| Weight (kg) | | 38.8 ± 6.9 |
| | Disease | |
| Acute Lymphoblastic Leukemia | | 6 (3 patients) |
| Acute Myeloid Leukemia | | 3 (2 patients) |
| Neuroblastoma | | 1 |
| Ewing s Sarcoma | | 4 (2 patients) |
| Total | | 14 (8 patients) |

Data is expressed as mean±SEM. Number of cycles assessed with respect to cancer diagnosis is expressed as the number of cycles assessed (number of patients contributing to cycles assessed).

TABLE 7

Chemotherapy regimens administered to 8 evaluable patients in cycle 1 and/or cycle 2 of testing.

| Patient | Cycle 1 Chemotherapy | Cycle 2 Chemotherapy |
| --- | --- | --- |
| 1 | Vincristine; Cyclophosphamide; Doxyrubicin | Vincristine; Cyclophosphamide; Dactinomycin |
| 3 | Methotrexate; Vincristine | Methotrexate; Vincristine |
| 5 | Melphalan; Carboplatin; Etoposide | N/A |
| 7 | Methotrexate; Vincristine | Methotrexate; Vincristine |
| 8 | Methotrexate; Vincristine; 6-Mercaptopurine | Methotrexate; Vincristine |
| 11 | Cytarabine; Idarubicin; Etoposide | N/A |
| 12 | Cytarabine; Thioguanine | Melphalan |
| 13 | Vincristine; Cyclophosphamide; Doxyrubicin | Etoposide; Ifosfamide; Carboplatin |

Patients received HD-chemotherapy in all cycles that were assessed. Where N/A represents patents where only one cycle of chemotherapy was assessed as treatment had ceased from that point.

Experimental Design

All subjects were required to fast overnight prior to testing and for a minimum of four hours of the testing period. Only small amounts of water were permitted during testing and a small meal was permitted after 4 hr. Physical activity was kept to a minimum. Weights and heights were recorded on the date of each test in all subjects.

Control testing: 26 control subjects performed two complete tests (comprised of SIP and SBT) of 5 hr in duration. Both complete tests were carried out on 2 separate occasions with a minimum of one week between each. The means of the SIP and SBT were calculated for the two separate occasions (test 1 and test 2), as well as a combined mean of the two occasions ($T_M$).

Patient testing: Patients were asked to take part throughout one cycle of chemotherapy, and if possible, to repeat the testing throughout a second cycle. A course of four or five complete tests were conducted throughout a cycle of chemotherapy. Baseline test was performed up to 5 days before administration of HD-chemotherapy (Test 1); day 1 test was performed within 24 hrs following administration of HD-chemotherapy (Test 2); 3-5 days after chemotherapy (Test 3); 6-9 days after chemotherapy (Test 4). Test 5, was only performed if mucositis had been diagnosed clinically after test 4 had been performed and was completed before a new cycle of chemotherapy had commenced. Eight evaluable cancer patients contributed to the final assessment of 14 cycles of chemotherapy. Each cycle of chemotherapy was assessed individually as mucositis can develop in one cycle of chemotherapy independent of another. The development of mucositis in a cycle of chemotherapy was independently assessed by an oncology clinician (See below). Patient group who did not develop mucositis clinically in a cycle of chemotherapy have been labeled "no mucositis" and group that did develop mucositis in a cycle of chemotherapy labeled "mucositis".

Clinicians' Assessment Criteria for Patients with Suspected Mucositis:

1. Assess Oral Mucosa
   a) has the oral mucosa turned from a pink appearance to a more white appearance?
   b) Is there ulcers? If so how many and where are they situated? (indicates severity)
   c) Is there additional inflammation with oral ulcers? (indicates infection)
   d) Does the patient have gingivitis?
   e) Is there herpes ulceration—clinically seen anteriorly in the oral cavity?
2. Assess patients nasal passage—if possible.
3. Assess perineal epithelium around the anus—is there swelling, tenderness, pain, ulcers?
4. Abdominal examination:
   a) abdominal bloating
   b) abdominal distension
   c) diarrhoea? frequency? consistency?
   d) Pain
   e) Bowel sounds Combination of these symptoms, etc, determine the severity of mucositis. Currently there is no adequate "score" for the diagnosis of mucositis.

Small Intestinal Permeability (SIP)

All subjects voided their bladder (pre-test sample) prior to commencement of testing. A L/R drink, comprising of 7.5 mL Lactulose syrup (Dupholac, SOLVAY-DUPHOV, B.V., Holland), and 1.1 g L-Rhamnose (SIGMA, Sigma-Aldrich, Germany) mixed with 92.5 mL water, was ingested (t=0 hr). All subsequent urine voided during the next five hours was collected. If subjects were unable to void their bladder at t=5 hr, the next urine voided was collected. All urine was pooled for each subject on the respective test day, and stored in a container containing 0.1 mL of 10 g/L thiomersal as preservative. Urine volumes were measured then aliquotted (12 mL) and stored at −20° C. until analysis.

Sucrose Breath Test (SBT)

At t=1.5 hr (SBT baseline) into the SIP test, subjects exhaled into 3×10 mL glass tubes (Exetainer, Labco Limited, High Wycombe, England) using a straw, ensuring that samples contained breath from end-expiration. Following the SBT baseline sample, subjects intermediately ingested 20 g $^{13}$C-Sucrose (AnalaR, BDH, MERCK, Pty Ltd, Victoria, Australia) dissolved in 100 ml water. Triplicate breath samples were then taken every 15 mins for 3 hours. Breath $^{13}CO_2$ was analyzed to determine small intestinal digestive/absorptive capacity (Example 1).

Urinary Permeability Analysis 2 mL samples of aliquotted urine were treated with half a volume of mixed bed ion exchange matrix, twice (Amberlite MB-1 resin; BDH; Rohm & Haas Company; USA), then passed through a 0.2 μm filter. Samples were diluted to 1/10 or more, depending on urine sugar concentrations[23]. Lactulose and rhamnose concentrations in urine were determined by high performance liquid chromatography (HPLC)(Dionex DX500 system; Dionex Corporation; Sunnyvale, Calif., USA) at the Royal Darwin Hospital, Darwin, Australia. Briefly, carbohydrates were separated on a Carbopac PA10 anion exchange column, with matching guard column.

Elution of the monosaccharides was achieved with an isocratic eluent of 40 mM NaOH for the first 7 min. At 7.01 min this was stepped up to 100 mM NaOH for disasccharide elution. After 19 min the column was washed for 5 mins with 200 mM NaOH. A complete run took 29 min at a flow rate of 0.8 mL/min. Chromatograms were integrated and plotted using Peaknet 4.3 software[23].

Total urinary excretion of the sugar probes were calculated for each subject, and results were expressed as the percentage of L/R to eliminate confounding factors such as gastric emptying, intestinal transit and renal clearance as previously described[23-25].

Where $L/R$ ratio $(\log_{10})$ =

$$((\text{Lactulose \% Recovered} / \text{Rhamnose \% Recovered}) \times 100) \log_{10}$$

Breath $^{13}CO_2$ Analysis 10 ml breath samples were analyzed for $^{13}CO_2$ using an isotope ratio mass spectrometer (IRMS; Europa Scientific, ABCA 20/20, Crewe, United Kingdom) equipped with a V410 data collection system. Results were presented as a delta value, representing the ratio of $^{13}C/^{12}C$, in comparison to the calcium carbonate international primary standard, Pee-Dee Belemnite limestone (South Carolina, U.S.A.) (Matthes and Hayes (1979), which is read in the sample as parts per thousand with high accuracy (Ghoos et al., 1993).

$^{13}CO_2$ data is expressed as percentage cumulative dose of $^{13}C$ (% CD). Where % Cumulative Dose of $^{13}C$ is equal to:

$$\% \ ^{13}C \ \text{cumulative} \ dose_{ti+1} = \% \ ^{13}C \ \text{cumul} \ Dose_{ti} + \left( \frac{\% \ ^{13}C \ dose_{ti} + \% \ ^{13}C \ dose_{ti+1}}{2} \right) \times 1/n$$

n=number of samples/hr ti=time i $^{13}CO_2$ analysis takes into account each subject's height and weight (Body Surface Area (Haycock et al., 1978)), as described by Ghoos et al., (1993). The first 90 min of $^{13}CO_2$ excretion was used as a cut-off point for SBT analysis as small intestinal transit time is approximately 90 min. In addition, it has been shown that after this point colonic fermentation of malabsorbed $^{13}C$-Sucrose, as seen in gut compromised individuals, can cause a rise in $^{13}CO_2$ in the breath, thus producing false positives (Pelton et al., 2002).

Statistical Analysis

A One-Way ANOVA in conjunction with a Fisher-LSD post-hoc test, was used to determine significance for all analyses between controls (n=26), no mucositis (n=8) and mucositis (n=6) groups. A Two-Way ANOVA was used to factor in sex and age in control subjects with respect to test 1 (T1) and test 2 (T2) for SIP and SBT. L/R ratio data was log transformed to normalize the data. Statistical significance was considered if p<0.05. All data have been expressed as mean±standard error of the mean (SEM).

Results

Controls

Mean L/R ratios for T1 and T2 of the 26 control subjects were 0.572±0.023 and 0.5624±0.029, respectively. No significant difference was observed between the two tests. Sex and age had no significant effect on the outcome of L/R ratio for T1 and T2. The combined mean $(T_M)$ average for L/R was 0.57±0.021 and the range was 0.35-0.79 (±2 standard deviations (SD)).

Mean % CD of $^{13}C$-sucrose (0-90 mins), for T1 and T2 (n=26), were 8.48±0.39 and 8.49±0.43, respectively. No significant difference was observed between T1 and T2. Sex and age did not affect the outcome of % CD of either T1 or T2. The % CD of $^{13}C$-sucrose of $T_M$ was 8.48±0.33 when averaged and the subsequent range was 5.06-11.90 (±2 SD).

Patients

Of the 14 complete cycles of chemotherapy that were assessed, six patients developed mucositis in a cycle of chemotherapy (43%) and eight did not (57%), as independently diagnosed by a clinician. At day 6-9 after chemotherapy (Test 3), two patients who developed mucositis, in a cycle of chemotherapy were unable to complete test procedures due to the mucositis severity (n=4).

There were no differences in L/R permeability ratios between the three groups (controls, no mucositis or mucositis) at baseline. SBT % CD was significantly lower in the mucositis group compared to controls and the no mucositis group (p<0.05) at baseline (Table 8).

TABLE 8

Assessment of small intestinal barrier and absorptive function of all subjects at baseline.

|  | SIP L/R ratio ($\log_{10}$) | SBT % CD (0-90 min) |
|---|---|---|
| Controls | 0.57 ± 0.022 | 8.49 ± 0.33 |
| No Mucositis | 0.54 ± 0.064 | 9.27 ± 0.54 |
| Mucositis | 0.65 ± 0.110 | 5.60 ± 1.54*α |

SIP and SBT at baseline for controls (n = 26), no mucositis group (n = 8) and mucositis group (n = 6). Data have been expressed as mean ± SEM, where * denotes significant difference to HC p = 0.004 and - denotes significant diffence to no mucositis group, p = 0.002.

At day 6-9 after chemotherapy, the mucositis group (n=4) had a significantly elevated L/R ratio (70%), compared to the no mucositis group, (p=0.03). The mucositis group was above the "normal" range at day 6-9 after chemotherapy, while the no mucositis group was within the normal range of the healthy controls (FIG. 10).

A significant (p<0.05) decrease in % CD $^{13}C$-sucrose (0-90 min) in the mucositis group compared to the no mucositis group was observed at all time points tested (FIG. 11). The mucositis group had a 39%, 43%, 68% and 54% decrease of excreted $^{13}CO_2$ ($^{13}C$-sucrose) compared to the non mucositis group at baseline, day 1, day 3-5 and day 6-9, respectively. The mucositis group was below the "normal" range of the controls from day 1 and had not returned to normal by day 6-9 after chemotherapy, while the no mucositis group stayed within the range.

Discussion

It has been shown previously that mucositis is a common side-effect of chemotherapy, where it occurs in up to 60% of cancer patients undergoing chemotherapy treatment. Mucositis is characterized by ulcerating lesions in the gastrointestinal (GI) tract as a result of chemotherapeutic agents affecting cell-lines with a rapid cell-turnover rate, such as the GI epithelium (Morelli et al., 1996; Ijiri and Potten, 1983; Ikuno et al., 1995). It has been found in the small intestine that chemotherapy causes villus blunting, shallow crypts and hypoproliferation of crypt cells, due primarily to an increase in apoptosis and a decrease in proliferation (Iriji and Potten, 1983; Ikuno et al., 1995; Xian et al., 2000; Keefe et al., 2000).

Patients who develop ulcerating lesions in the small intestine, as a result of chemotherapy treatment, are unable to be assessed using the current invasive biopsy technique as they commonly present with low platelet and white blood cell counts. Thus increasing the risk of GI bleeding and bacterial translocation/infection (Keefe, 1998; Keefe et al., 2000). Therefore, the aim of this example was to non-invasively assess small intestinal status in healthy children and children with cancer receiving chemotherapy, using non-invasive markers (Menzies et al., 1979) to determine whether these tests could detect intestinal changes attributed to patients who developed mucositis over a cycle of chemotherapy.

This pilot study demonstrated that the SIP and SBT are capable of non-invasively assessing small intestinal health and dysfunction in healthy children and in children with cancer undergoing chemotherapy, and detected compromised small intestinal function in children who developed mucositis clinically in a cycle of chemotherapy.

This example establishes a "normal" range of the SBT in response to the ingestion of 20 g $^{13}$C-Sucrose by measuring breath $^{13}CO_2$. Sucrose is catalyzed by sucrase, a brush-border enzyme, in the small intestine into its constituent monosaccharides, fructose and glucose, in the healthy individual. Subsequent metabolism of these products in the liver leads to the production of $CO_2$, which is excreted in the breath. This can be detected and measured using simple IRMS analysis (Example 1, Schoeller et al., Koetse et al., 1999). It has been shown that sucrase activity is the rate-limiting factor in this technique, where the decreased level of sucrase activity, and the subsequent metabolism of its products, leads to a decrease in $^{13}CO_2$ excreted in the breath (Butler et al., 2002). Previous studies have utilized the $^{13}$C-lactose breath test as a marker of small intestinal damage, however 80% of non-Caucasians exhibit an age-related low lactase activity (Koetse et al., 1999). In comparison, only 0.2% of the population present with a genetic sucrase deficiency (Gray et al., 1976). Thus, the $^{13}$C-sucrose breath test is a reliable and superior prognostic enzyme of mucosal damage (see example 1).

The SBT is capable of detecting abnormal small intestinal function 24 hr after chemotherapy administration in cancer patients with subsequent development of mucositis. A degree of variability is observed in the "mucositis" group over a cycle, which is most likely due to differing factors, such as duration of administration and doses, of the chemotherapeutic drugs on the individual, and thus its affect on the GI epithelium. Patients who developed mucositis in a cycle of chemotherapy have a significantly lower $^{13}CO_2$ output. This is seen at baseline and continues to be significantly depressed at day 6-9. The common length of time between the beginning of one cycle of chemotherapy and the next is approximately 14 days, it is possible that the depression observed at baseline could be indicative of a carry-over affect from the previous cycle of chemotherapy. This rationale has been addressed in a study by Keefe et al., (2000), where small intestinal morphometric severity scores, as measured by villus area, crypt length and mitotic count, in naive, adult cancer patients, did not return to pre-treatment values until 16 days after chemotherapy treatment.

The present example observed a similar "normal" range for L/R ratio as studies previously reported when utilizing an identical analytical technique (Xian et al., 2000; Kukuruzovic et al., 1999; Brewster et al., 1997). It should be noted however, that the range derived from the healthy controls in this study is broader than that of these previous studies. This is likely attributed to the fact that these studies were carried out in children less than three years of age (Behrens et al., 1987; Saltzman et al., 1995), were performed in a location where geographical gastroenteritis is common (Kukuruzovic et al., 1999), and only ingested 1.0 g of rhmanose as opposed to 1.1 g. Studies that have utilized varied analytical techniques however, have derived a range similar to this study for the same age group (Menzies et al., 1979).

Children with cancer who developed mucositis during a cycle of chemotherapy can be detected using SIP, as demonstrated by a significantly elevated L/R ratio on days 6-9 compared to the cancer patients undergoing chemotherapy who did not develop mucositis. This indicates that barrier function may become compromised due to villus atrophy and/or an alteration in tight junction integrity. Previous studies demonstrated that a decrease in monosaccharide permeation is a sign of villus atrophy, and an increase in disaccharide permeation indicative of "leaky" tight junctions (Keefe et al., 1997; Pearson et al., 1984; Sundström et al., 1998). Tight junction status has been studied in adult cancer patients, where it was noted under electron microscopy that the percentage of tight unctions that were open increased in cycle of chemotherapy from pre-treatment chemotherapy values (Keefe et al., 2000).

As a result of villus blunting and a decreased capacity of crypts to induce villus renewal, compromised function has been observed in the SIP and SBT. This pilot study has shown that even though mucositis is commonly clinically observed 7 days after chemotherapy administration (Sonis, 1998; Keefe et al., 2000), that small intestinal changes had occurred before this point. This is most likely attributed to the fact that the current method of diagnosis, as documented in studies worldwide (Sonis et al., 1999; Turhal et al., 2000; Chang et al., 2000), is primarily based on oral and anal assessment criteria, and patient symptoms. However, SBT results suggest that the current method of assessing mucositis is not sensitive enough, as small intestinal damage occurs well in advance to the common diagnosis time of 7-10 days when mucosal changes become visible. Indicating that the SBT should be implemented into clinical practice to aid in mucositis diagnosis.

Another important implication of this stexample is the future possibility to maintain "quality of life" in these patients. It is well documented that quality of life is greatly diminished, or questioned, in children diagnosed with cancer (Dodd et al., 2001). It is difficult enough to contend with the life changes associated with cancer treatment, especially in children, such as hair loss, hospitalization and treatment itself, without having to deal with a severe side-effect, such as mucositis (Feld, 1997). The findings of this study leads to the question of when to intervene with pharmaceutical or nutritional products when mucositis develops? Currently, a preventative or intervention product is not available clinically, however, extensive research is underway which may lead to the availability of such a product (Henriksson et al., 1995). Thus, employing the SBT for high-risk cycles at baseline, d1 or d3-5, and ensuing abnormal results, could lead to early administration of intervention products for mucositis in patients throughout cancer treatment, as opposed to waiting for symptoms to be visibly observed. This may in fact minimize the severity and/or the duration of mucositis, or even prevent its occurrence and maintain a decent quality of life.

It is important to note for the SBT that for sensitivity and specificity to be maintained, or in fact improved, that the administration of a standardized diet, comprising of foods that are not naturally enriched with $^{13}$C for 3-5 days preceding the test might be beneficial. Also, the addition of a second breath test, the hydrogen breath test, to be used in conjunction with the SBT, could be used to further confirm small intestinal damage. Where a rise in $H_2$ excretion in the breath would be indicative of the malabsorbed substrate, sucrose (Barr et al., 1978).

It is also interesting to note that a significantly elevated L/R ratio, in relation to compromized small intestinal barrier function, has been observed in patients with other gastrointestinal disorders such as active Crohn's and celiac disease (Menzies et al., 1979; Smecuol et al., 1997). Similarly it has been documented that these patients can also present with decreased brush-border enzyme activities (Nieminen et al., 2001; Arvanitakis, 1979; Cummins et al., 1991; Duncan et al., 1994), such as sucrase, as detected by biopsy. Therefore, it is proposed that the SBT could be applied to aid in diagnosis for these conditions, and thus potentially eliminate a costly and invasive procedure.

Interventions, either nutritional, such as Vitamin supplements (Kokkonen et al., 2002) or pharmaceutical, such as keratinocyte growth factor (Goodlad et al., 2000) or epidermal growth factor (Huang et al., 2001), are being researched for mucositis. The SBT could therefore be employed as a marker/monitor to determine when is the best time to intervene for the individual patient, and efficacy of improving GI symptoms.

EXAMPLE 7

Folinate Inhibition of Methotrexate Treated Rats

Methods

Experimental Design

Sixteen female SPF Dark Agouti rats were housed in individual metabolism cages and were given ad libitum access to a semi-synthetic casein based diet and fresh water. Food and water intakes and body weights were measured daily. They were given two injections of MTX (1.5 mg/kg i/m) at 0 and 24 hrs. Calcium folinate was added to the drinking water of eight rats (10 mg/m$^2$) 2 hours prior to, and during MTX injections. Eight rats were given MTX but no folinate treatment, and four control rats were given no treatments. Four rats from each treatment group were killed at 72 hours, and the other four at 120 hours, after initial chemotherapy. SBT were undertaken before chemotherapy, and at 52 and 100 hours after initial chemotherapy.

At the appropriate times, rats were anaesthetised with halothane, cardiac blood samples collected and the animals were killed by cervical dislocation. The small intestine was emptied, flushed with chilled saline and weighed. Samples were collected into formalin from each of the proximal jejunum for histological assessment, and from the jejunum into liquid nitrogen for sucrase and myeloperoxidase determinations.

Sucrose Breath Test

Breath $^{13}CO_2$ levels are indicative of sucrase activity in the small intestine. SBTs were undertaken before and after chemotherapy.

Rats were fasted for 3 hrs and placed in the collection chambers for 15 minutes to acclimatise and baseline samples collected into exetainers.

Rats were gavaged with 1.0 ml of a sucrose solution containing 1 g/ml of naturally enriched $^{13}C$-sucrose.

Breath samples were collected at 30, 60 and 90 minute time intervals after gavage and analysed for $^{13}CO_2$ by isotope ratio mass spectrometry (PDZ-Europa ABCA).

Analytical Techniques

Sucrase activity was measured using a modification of the glucose oxidase method for estimation of the breath glucose concentration (Dahlqvist, 1968).

Results

The food intakes and body weights of rats not given folinate decreased after chemotherapy treatment (data not shown). SBT results show that at 52 hrs after MTX treatment folinate administration attenuates mucosal damage (FIG. 12). FIG. 13 shows a significant decrease in disruption to the sucrase activity in the folinate group compared to no folinate (p<0.0012 at 52 hours, p<0.0136 at 100 hours). This data is supported by jejunal sucrase activity results (FIG. 14) and the prevention of an elevation in tissue MPO (FIG. 15). At 72 hours the MTX-treated no folinate group was significantly different to folinate and control groups (p<0.01).

Summary

Treatment of rats with MTX without folinate resulted in a significant 20% reduction in food intake from $t_0$ to 96 hours after treatment (data not shown).

Body weights of rats given MTX without folinate decreased after chemotherapy

The inflammatory marker myeloperoxidase was significantly higher in MTX treated rats not given folinate at 72 hours.

SBT showed small intestinal function was impaired as a result of chemotherapy

Folinate administration prevented the reduction in jejunal sucrase activity observed in non-folinate MTX-treated rats.

Measurement of villus heights indicated that structural damage was attenuated when folinate was administered orally.

Conclusions

Calcium folinate totally prevented damage to the small intestinal mucosa as measured by sucrase activity, MPO levels, histological changes and sucrose breath testing. The SBT is the only technique used in this study that is non-invasive and provides a simple and valuable method to monitor dysfunction in the small intestine. SBT provides an integrated measure of small intestinal function and can be used to assess the efficacy of preventative or ameliorative adjunctive therapies. In the future the SBT may provide an objective way to tailor chemotherapy regimens to optimise nutritional status during treatment, potentially lessening the debilitating impact of chemotherapy.

EXAMPLE 8

Mucositis in 5-fluorouracil Treated Rats

Chemotherapy-induced intestinal mucositis is a serious side effect in cancer patients, particularly those receiving antimetabolite drugs. The sucrose breath test (SBT) is a novel technique to assess in vivo the function of the small intestine during damage and repair. We now describe a rat model of chemotherapy-induced mucositis using a single injection of 5-fluorouracil (5-FU).

Methods

Ten female Dark Agouti rats were injected intraperitoneally with 150 mg/kg 5-FU; three rats there killed at 48, 72 and four at 96 hours after 5-FU treatment. Two control rats were not treated with 5-FU. Sucrose breath tests (SBT) were undertaken before chemotherapy and prior to sacrifice by measuring released $^{13}CO_2$ in the breath after gavages of $^{13}$C-sucrose as an indicator of small intestine (SI) sucrase function. Tissue samples were collected from SI for sucrase enzyme determinations and histological assessment from the jejunum and ileum.

Results

Food intakes fell from 11.1±0.3 g/rat/day to 5.3±0.4 g 24 hours after 5-FU injection, were lowest 72 hours after injection (4.7±0.7 g) and began to increase at 96 hours (6.4±0.8 g). SBT indicated loss of enzyme function was most severe at 76 hours post-chemotherapy; area under curves (AUC) of production rates of $^{13}CO_2$ were significantly lower than pre-chemotherapy AUC at 72 hours (7.02±0.16 and 2.02±0.25 respectively; P<0.01, non-parametric ANOVA). Ileal sucrase activity fell from normal levels of 54.9±0.9 to 7.52±0.82 nmol glucose/min/cm at 72 hours, with levels beginning to increase at 96 hours post-chemotherapy. Histological severity scores of jejunal and ileal tissue indicated most severe damage occurred at 48 hours (medians 13 and 17 respectively), with the damage mainly confined to the crypts. Severity scores were 8 and 12 at 72 hours, and 5 and 8 at 96 hours for jejunum and ileum respectively.

Conclusions

The SBT and sucrase enzyme measurements indicate maximum functional impairment occurred at 72 hours post-chemotherapy. The most severe histological damage occurred in the crypts at 48 hours post-chemotherapy. SBT is a valuable in vivo method of assessing SI function. Single-dose 5-FU treatment provides a simple model of intestinal mucositis suitable for mechanistic and intervention studies.

REFERENCES

Arvanitakis (1979) Digestion; 19(4):259-66.
Barr et al., (1978) Pediatrics; 62:393-401.
Behrens et al., (1987) Am J Clin Nutr; 45:1433-41.
Bradford (1976) *Analytical Biochemistry;* 72: 248-254.
Brewster et al., (1997) Arch Dis Child; 76:242-8.
Butler et al., (2002) Gastroenterology; 122(Suppl 4):A-72.
Chang et al., (2000) Cancer; 88(9):64-71.
Cummins et al., (1991) J Gastroenterol Hepatol; 6:53-7.
Dahlqvist (1968) *Analytical Biochemistry;* 22: 99-107.
Davidson and Robb et al., (1985) *Journal of Pediatric Gastroenterology and Nutrition;* 4: 381-387.
Dodd et al., (2001) *J Pain Symptom Manage;* 21(6):498-505.
Duncan et al., (1994) Scand J Gastroenterol; 29:1111-6.
Erdman et al., (1991) *Journal of Pediatric Gastroenterology end Nutrition;* 13: 360-366.
Feld (1997) Support Care Cancer; 5:371-5.
Fiedorek et al., (1991) *Journal of Pediatric Gastroenterology and Nutrition;* 12: 237-242.
Ghoos et al., (1993) Breath tests in gastric emptying and transit studies: technical aspects of $^{13}CO_2$-breath tests. In: Janssens J, ed. Progress in Understanding and Management of Gastro-intestinal Motility Disorders. Belgium: Katholieke Universiteit Leuven, 1993; 169-80.
Goodlad et al., (2000) Regul Pept 2000; 87:83-90.
Gray et al., (1976) N Engl J Med; 294:750-3.
Hanozet et al., (1981) *J Biol Chem* 256; 370-4711.
Haycock et al., (1978) J Pediatr; 93:62-6.
Hiele et al., (1988) *Journal of Laboratory and Clinical Medicine;* 112: 193-200.
Howarth et al., (1996). *Journal of Nutrition;* 126: 2519-2530.
Huang et al., (2001) Am J Physiol; 282:G432-G42.
Ijiri and Potten (1983) Br J Cancer; 47:175-85.
Ikuno et al., (1995) J Natl Cancer Inst; 87(24):1876-83.
Keefe et al., (1997) Clin Sci; 92:385-9.
Keefe (1998) MD Thesis, University of Adelaide, Adelaide, South Australia.
Keefe et al., (2000) Gut; 47(5):632-7.
Klein and Klein. (1985) *Journal of Pediatric Gastroenterology and Nutrition;* 4: 9-19.
Koetse et al., (1999) *Scandinavian Journal of Gastroenterology;* 34: 35-40.
Kokkonen et al., (2002) Pediatr Hematol Oncol; 19:181-92.
Kukuruzovic et al., (1999) Arch Dis Child; 81:304-8.
Lembcke et al., (1989) *Klin Wochenschr;* 67: 568-575.
Maclean et al., (1983) *Pediatric Research;* 17: 629-633.
Matthews and Hayes (1979) Stable Isotopes, 3rd International Conference 1979:95-104.
Menzies et al., (1979)*The Lancet;* 2:1107-9.
Morelli et al., (1996) Cancer Res; 56:2082-5.
Nieminen et al., (2001) Scand J Gastroenterol 2001; 36(5): 507-10.
Perman et al., (1978). *Journal of Pediatrics;* 93: 17-22.
Pearson et al., (1984) Arch Dis Child; 59:460-5.
Pelton et al., (2002) Gastroenterology; 122(Suppl 4):A-545-6.
Pledger et al., (1988) Eur J Pediatr; 147:123-7.
Renes et al., (1997) *Journal of Pediatric Gastroenterology and Nutrition;* 24: A41.
Ruppin et al., (1988) *Gastroenterology;* 95: 93-99.
Saltzman et al., (1995) J Am Geriatr Soc; 43:160-4.
Schoeller et al., (1980). *American Journal of Clinical Nutrition;* 33: 2375-2385.
Shirazi and Beechley. (1991) *Journal of Physiology;* 437: 691-698.
Smecuol et al.,(1997) Gastroenterology; 112:1129-36.
Sonis (1998) Oral Oncol; 34:39-43.
Sonis et al., (1999) Cancer; 85(10):2103-13.
Stellaard et al., (1998) Standardization and accuracy of breath tests. In: Perri F. and Andriulli A., eds. Clinical application of breath tests in gastroenterology and hepatology.Rome:International University Press, 1998:13-16.
Sundström et al. (1998) Eur J Haematol; 61:250-4.
Taminiau et al., (1980). *Gut;* 21: 486-492.
Turhal et al., (2000) Support Care Cancer; 8:55-8.
Vanderhoof et al., (1990) *Gastroenterology;* 98: 1226-1231.
Verburg et al., (1997) *Journal of Pediatric Gastroenterology and Nutrition;* 24: A33.
Xian et al., (2000) Br J Cancer; 82(4):945-52.

The invention claimed is:

1. A method of assessing the state of the lining of the small intestine in an animal said method comprising
taking an initial breath sample,
administering a labelled test substrate to said animal, wherein said test substrate is acted upon by an enzyme to produce $CO_2$ and wherein said test substrate is selected from the group consisting of sucrose and maltose,
taking one or more further breath samples after administering said labelled test substrate,
ascertaining and comparing the level of labelled carbon dioxide in the initial breath sample and the further one or more breath samples and calculating the change in labelled carbon dioxide after ingestion of the test substrate wherein a decrease in the labelled $CO_2$ level between said initial sample and said further breath sample(s) is indicative of damage to the small intestine.

2. The method of claim 1 wherein the decrease in the labeled $CO_2$ is indicative of damage caused to the small intestine by gastroenteritis.

3. The method of claim 2 wherein the decrease in the labeled $CO_2$ is indicative of damage caused to the small intestine infectious agent.

4. The method of claim 1 wherein the decrease in the labeled $CO_2$ is indicative of damage caused to the small intestine by mucositis.

5. The method of claim 1 wherein the decrease in the labeled $CO_2$ is indicative of damage caused to the small intestine by chemotherapy.

6. The method of claim 1 or 5 wherein the animal is a human.

7. The method of claim 6 wherein the substrate is labelled with $^{13}C$.

8. The method of claim 7 wherein the label is $^{13}C$ and the ratio of $^{13}C$ to $^{12}C$ is measured.

9. The method of claim 1 wherein the substrate is sucrose.

10. The method of claim 1 wherein the substrate is maltose.

11. The method of claim 1 wherein the breath sample is taken 30 minutes or longer after initial injestion of the labelled test substrate.

12. The method of claim 1 wherein the breath sample is taken 60 minutes after initial injestion of the labelled test substrate.

13. The method of claim 1 wherein the breath sample is taken at between 45 minutes and 3 hours after injection of the labelled test substrate.

14. The method of claim 1 wherein additionally breath $H_2$ is measured.

15. The method of claim 1 wherein two or more further breath samples are taken.

16. The method of claim 15 wherein cumulative labelled $CO_2$ is ascertained.

17. The method of claim 1 wherein human or animal fasts before the labelled test substrate is administered.

18. The method of claim 1 wherein the human or animal is fed a standard diet before the labelled test substrate is administered.

* * * * *